United States Patent [19]
Vogeley, Jr.

[11] Patent Number: 5,324,228
[45] Date of Patent: Jun. 28, 1994

[54] METHOD AND APPARATUS FOR DETECTING AND TRIMMING FAT FROM MEAT PRODUCTS

[75] Inventor: Arthur W. Vogeley, Jr., Renton, Wash.

[73] Assignee: Frigoscandia Food Processing Systems A.B., Helsingborg, Sweden

[21] Appl. No.: 920,064

[22] Filed: Jul. 27, 1992

[51] Int. Cl.$^5$ ............................................. A22C 17/12
[52] U.S. Cl. ..................................... 452/158; 452/150
[58] Field of Search ............... 452/150, 157, 156, 155, 452/150, 159, 158

[56] References Cited

U.S. PATENT DOCUMENTS

| | | | |
|---|---|---|---|
| 3,800,363 | 4/1974 | Lapeyre | 17/52 |
| 4,549,453 | 10/1985 | Yazaki et al. | 83/365 |
| 4,557,019 | 12/1985 | Van Devanter et al. | 452/157 |
| 4,726,094 | 2/1988 | Braeger | 452/157 |
| 4,738,004 | 4/1988 | Lapeyre | 452/158 |
| 4,875,254 | 10/1989 | Rudy et al. | 17/61 |
| 4,962,568 | 10/1990 | Rudy et al. | 17/52 |
| 5,162,016 | 11/1992 | Malloy | 452/157 |

FOREIGN PATENT DOCUMENTS

0272030 9/1989 Fed. Rep. of Germany ...... 452/150

OTHER PUBLICATIONS

U.S. pat. appl. of Rudy et al., Ser. No. 07/701,893 filed May 17, 1991.
U.S. pat. appln. of James S. Tomlin, Ser. No. 07/772,309, filed Oct. 7, 1991.
"Can Robots Really Improve Production", Meat Processing, Nov. 1984, pp. 60, 61.

*Primary Examiner*—Willis Little
*Attorney, Agent, or Firm*—Olson & Olson

[57] ABSTRACT

Meat portioning apparatus supports meat products on an endless conveyor to move through a light stripe at which upstream and downstream cameras view the light stripe and convert spaced apart points of light to electric signals representing various magnitudes of light brightness, the magnitude of brightness above a predetermined minimum representing areas of peripheral fat on the meat product. The electric signals of magnitude above the predetermined minimum are utilized by a computer to control one or more line-type cutters to cut the meat product along lines which remove the areas of fat from the meat product.

12 Claims, 4 Drawing Sheets

METHOD AND APPARATUS FOR DETECTING AND TRIMMING FAT FROM MEAT PRODUCTS

BACKGROUND OF THE INVENTION

This invention relates to the reduction of animal and fish meat products to portions of desired weight or shape, and more particularly to the removal of peripheral fat from such meat products prior to portioning.

Processors of fish, poultry, beef and other meat products have various requirements as regards the amount and location of fat on finished cut product portions. The reduction of such meat products to smaller portions of predetermined weight or shape is accomplished by the method and apparatus described in U.S. Pat. Nos. 4,875,254 and 4,962,568 and copending patent applications Ser. No. 07/701,893 filed 17 May 1991 and Ser. No. 07/772,309 filed 7 October 1991, all of which have common ownership with the present invention. In said earlier developments the computer control was simply programmed to make cuts parallel to and a fixed distance in from the outer edges of the meat product to remove the peripheral fat. However, this procedure resulted in removing an excessive amount of "trim", i.e. lean meat in addition to peripheral fat. In large scale mass production, the lean meat thus removed with fat represents a significant loss of product.

SUMMARY OF THE INVENTION

The method and apparatus of this invention involves the illumination of a fillet of animal or fish meat as it is viewed by a video camera system, the surface areas of fat thus illuminated being brighter than the surface areas of lean meat. The video camera system is connected to a computer that converts the camera signals to electric digital signals representing illumination brightness, or greyscale levels. The computer compares the digital signals to a preselected threshold of greyscale level to ascertain the location and shapes of peripheral fat areas. The computer then controls the operation of a cutter mechanism to remove the areas of fat.

The principal objective of this invention is to provide a method and apparatus of the class described that overcomes the aforementioned limitations of the portioning method described hereinbefore.

Another objective of this invention is the provision of a method of the class described that is operable with the apparatus of the patents and patent applications described hereinbefore.

Still another objective of this invention is to provide a method and apparatus of the class described that is operable with use of incandescent light.

A further objective of this invention is the provision of a method of the class described that is operable with the apparatus of the patents and patent applications described hereinbefore to perform both fat removal and portioning to predetermined weight or shape.

The foregoing and other objects and advantages of this invention will appear from the following detailed description, taken in connection with the accompanying drawings of a preferred embodiment illustrating the method of this invention.

DESCRIPTION OF THE PREFERRED EMBODIMENT

The method of this invention is well suited for operation with the apparatus described in the patents and patent applications identified hereinbefore. Accordingly, the disclosures in said patents and patent applications are incorporated herein by reference.

Fat detection and trimming is accomplished, in accordance with this invention, by first collecting information on the product surface brightness. This is done simultaneously with the determination of product thickness, as accomplished preferably in accordance with the procedure disclosed in the patent application Ser. No. 07/772,309 identified hereinbefore.

Figure 1:
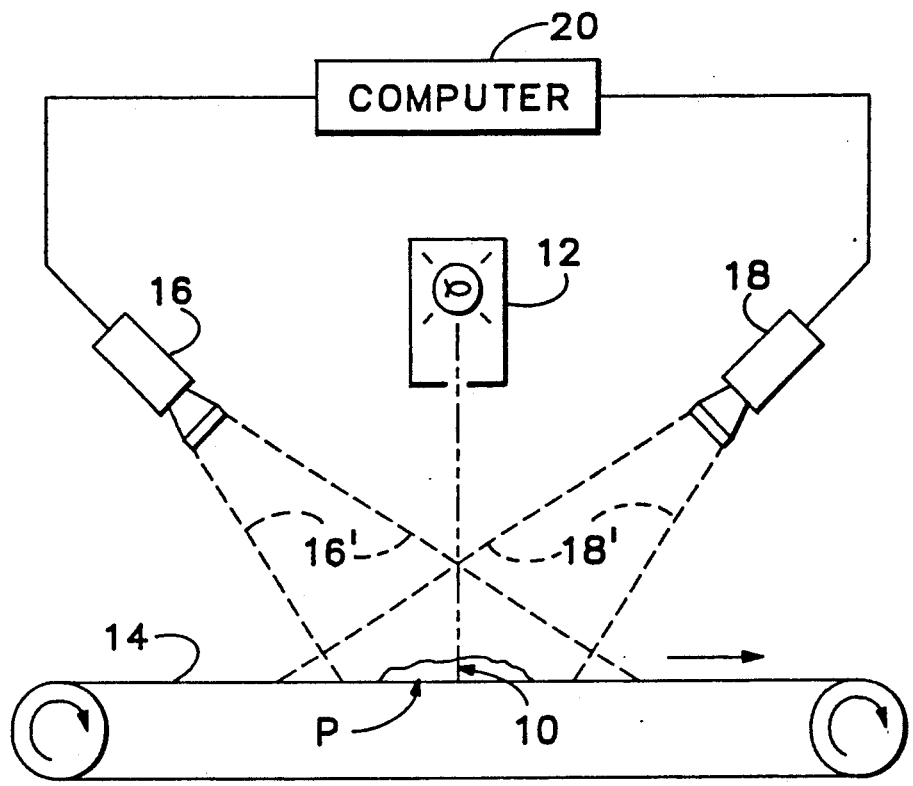
FIG. 1 is a side elevational view, in schematic form, of apparatus for performing the method of this invention.
Figure 2:
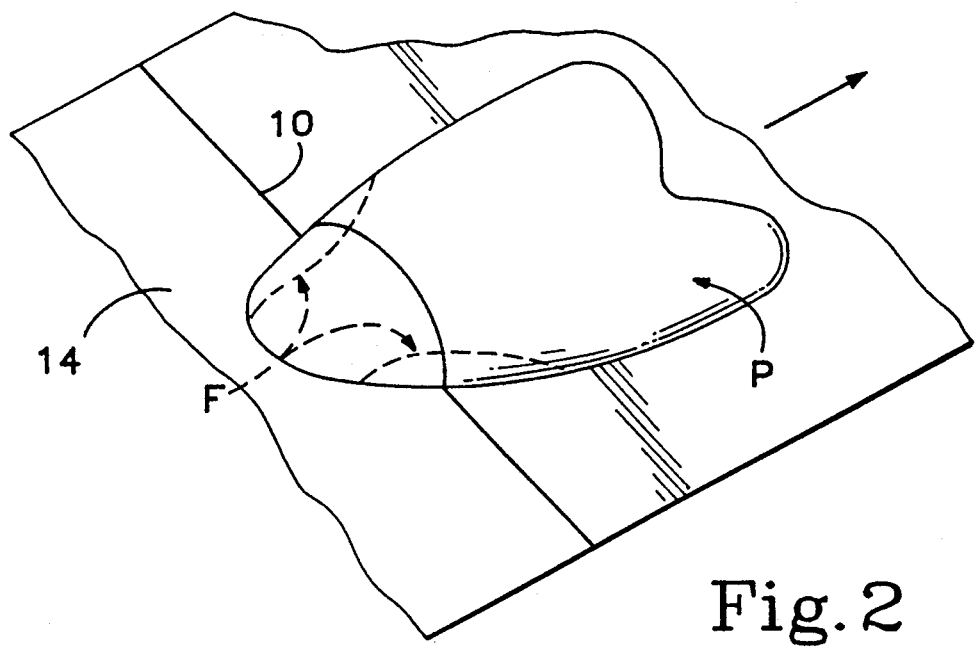
FIG. 2 is a perspective view of a chicken breast fillet, with areas of fat outlined by broken lines, moving on a supporting conveyor past a light stripe which spans the entire transverse dimension of the fillet.
Figure 3:
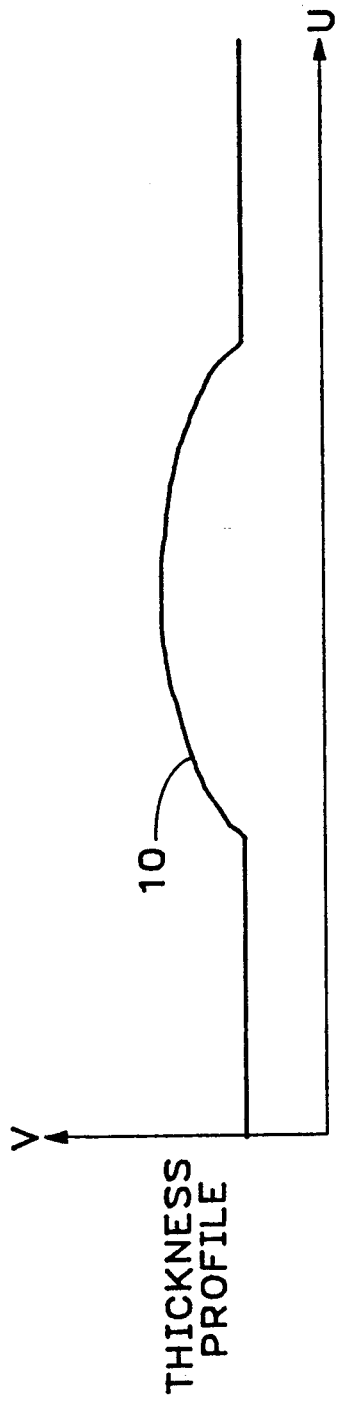
FIG. 3 is a graphic representation showing a plot of the thickness profile of the chicken breast of FIG. 2 at the position of the light stripe.

Briefly, such thickness determination is accomplished by measuring the vertical deviation of a light stripe 10 provided as a substantially vertical plane of light by a source 12, and projected crosswise on an endless conveyor belt 14 to span the product P as it moves through the stripe, as illustrated in FIGS. 2 and 3. Two video cameras 16 and 18, one mounted upstream and one downstream of the light stripe position, view the shape of the stripe on the surface of the product. The cameras are mounted at an angle of about 45° to the conveyor belt and their fields of view 16' and 18', respectively, are substantially perpendicular to the light stripe, as illustrated in FIG. 1. The use of two cameras enables each camera to "fill in gaps" in the field of view of the opposite camera, in cases where the stripe appears dim or is partially occluded by the product. Such use of two cameras is described in the patent application aforesaid.

The video cameras are connected to a computer 20 which is an integral part of the apparatus and functions to control the movement of one or more high pressure water jet, laser, or other line type cutters to reduce the meat product to desired portion weights or shapes. Dedicated "frame grabber" electronics within the computer convert the signals from the video cameras into digital picture elements 22 called pixels which can be processed by the computer. Pixels are identified by their horizontal (u) and vertical (v) axes coordinates within the field of view of each camera. Each pixel is an 8-bit value ranging from 0–255, expressing the greyscale brightness level at its particular position in the field of view.

The horizontal axis of the field of view of each camera lies roughly crosswise to the conveyor belt. Deflection of the light stripe appears as an approximately vertical displacement in the field of view, as illustrated in FIG. 3. To locate the light stripe, the computer searches vertically in the field of view for the brightest pixel, i.e. the one with the highest greyscale value, at a particular horizontal (u) coordinate. By performing this search at a selected set of horizontal coordinates, the computer accumulates a set of (u, v) pairs expressing the shape of the stripe as it intersects the product at one particular instant.

Figure 4:
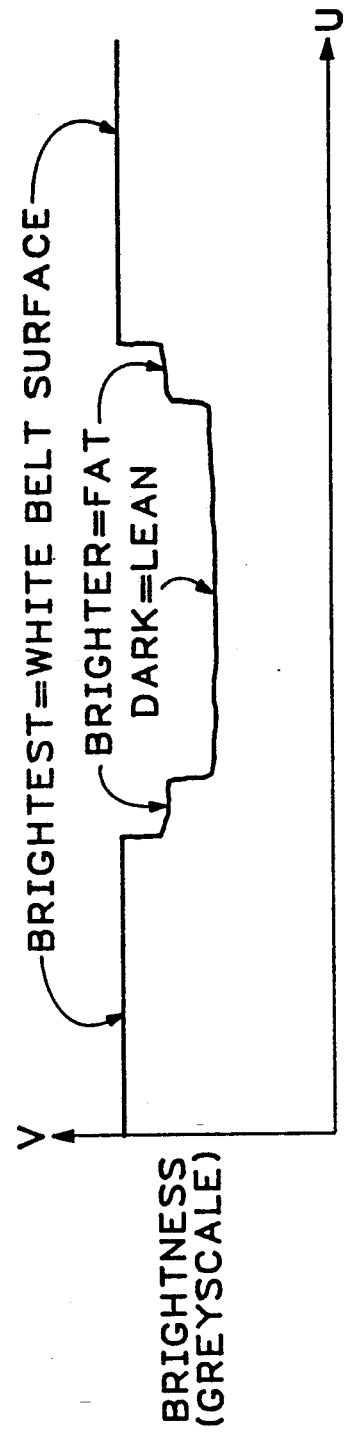
FIG. 4 is a graphic representation showing the plot of greyscale brightness along the light stripe of FIG. 3.

In accordance with this invention the computer is programmed to also record the greyscale values at the same set of coordinates, and it is these greyscale values that are the raw data used in detecting and trimming fat. FIG. 2 illustrates a chicken breast fillet product P with areas of fat F outlined in broken lines. Detection of these areas of fat relies upon the difference in overall optical brightness of a white or other form of light stripe between the areas of fat and lean on the surface of the product, as illustrated in FIG. 4. Fat typically appears brighter than lean meat, for substantially all forms of animal and fish meats.

In order for the calculations to keep up with the product flow rate on the conveyor belt, the computer searches the camera pixel data only at selected horizontal coordinates. For detecting and trimming fat it is desirable to select coordinates to include more points near the edges of the product. Initially examining a small number of coordinates establishes the approximate boundaries of the product. The computer then examines extra coordinates near the boundaries to increase the spatial resolution for the purpose of fat detection.

Each set of (u, v) coordinates is referred to as a slice, since it relates to the cross sectional profile of the product at a single point in time as it passes along the conveyor belt. It takes many slices, depending upon the length of the product being processed, to make up a complete thickness profile.

Figure 5:
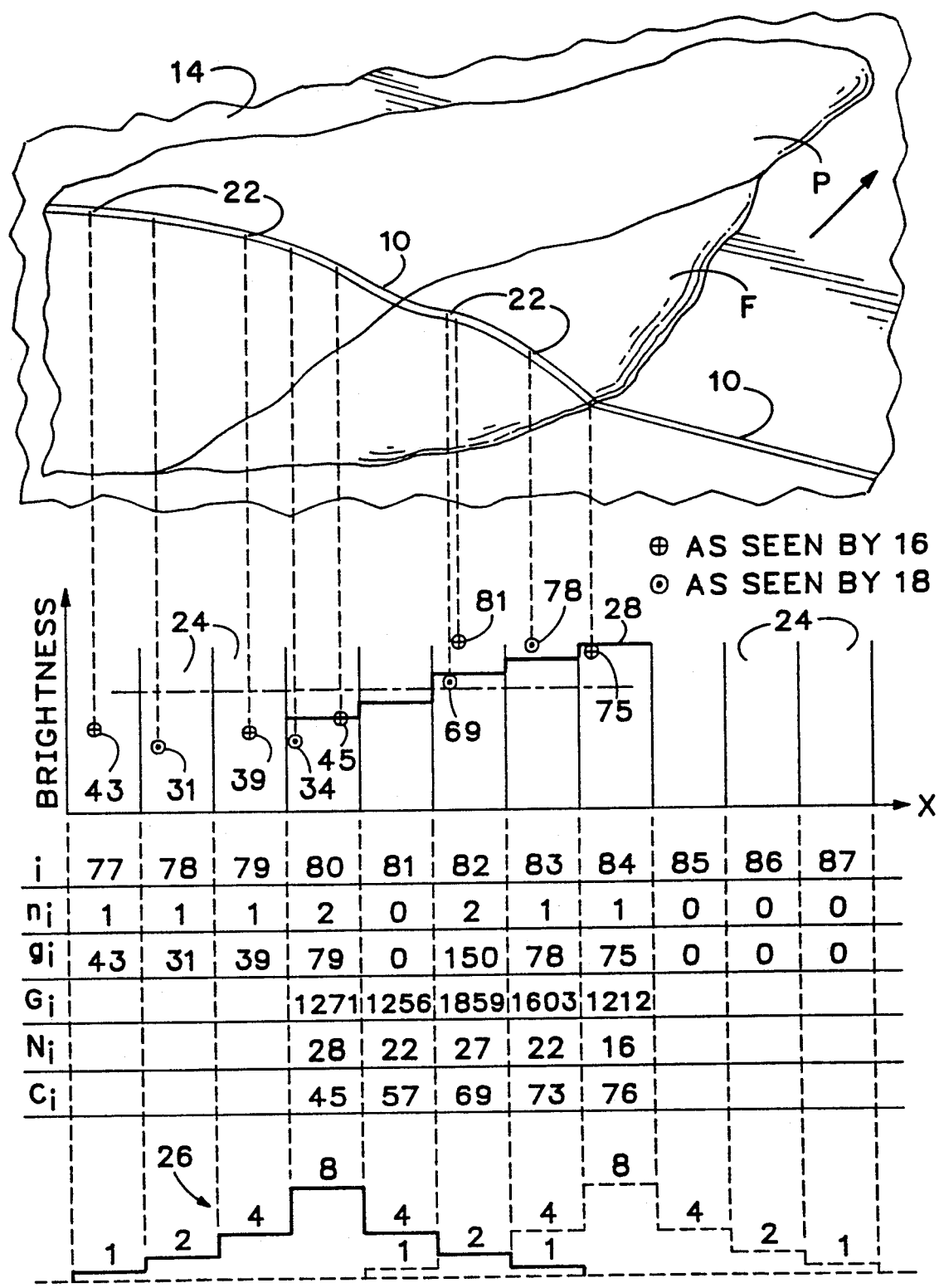
FIG. 5 is a perspective view of a portion of the chicken breast of FIG. 2, on an enlarged scale, together with a graphic representation of an exponential filter for use in determining composite greyscale values, and an exemplary representation of the accumulated greyscale sums and corresponding composite counts and greyscale values along a portion of the light stripe brightness greyscale of FIG. 4.

Each set of (u, v) coordinate pairs in a slice must be converted to physical coordinates aligned with the conveyor belt. Physical coordinates are (x, z) pairs where (x) is position in units such as millimeters across the belt and (z) is height in similar units above the belt. It is convenient to record height for discrete (x) ranges. Each discrete range is represented in the computer program as a bin. A precalculated look-up table is used to map a (u, v) coordinate pair into the appropriate bin for its (x) coordinate, and a height measurement (z). The look-up table converts points in the camera film plane into physical coordinates of points 22 on the light stripe 10 in the field of view of the camera. A bin accumulates the sum of the (z) measurements for measurements falling within an (x) coordinate range. Simultaneously, another paired bin 24, as illustrated in FIG. 5, accumulates the sum of the greyscale values associated with the measurements. For each pair of bins, a counter keeps track of the number of items accumulated.

Data from both the upstream and downstream cameras are accumulated into the same bins. At the end of this process, one bin in each bin pair contains the sum of zero or more (z) measurements and the other bin contains the sum of an equal number of associated greyscale values. The computer calculates an average (z) height measurement by dividing the sum of the measurements by the count of accumulated measurements. An interpolation procedure then determines height values for (x) coordinates where the bin happens not to contain any accumulated measurements.

The method for handling the accumulated greyscale data is central to detecting and trimming fat in accordance with this invention. Since greyscale data from both upstream and downstream cameras are accumulated into the bins, any given bin may contain no accumulated greyscale data samples, one or more samples from a single camera, or one or more samples from both cameras. A special filtering procedure takes this into account in calculating a composite greyscale value $C_i$ for the (x) coordinate range associated with a particular bin i, as illustrated in FIG. 5. The procedure makes use of a symmetrical exponential filter 26 (FIG. 5) with weighting coefficients which are powers of 2. The filter half-width W determines how many bins on either side of the central bin associated with a particular (x) coordinate are used in calculating a composite greyscale value. The half-width is chosen large enough to make it likely that at least one bin will contain a sum of a non-zero number of greyscale samples.

Since the sums in the bin are made up of greyscale samples from either camera, it is likely also that the composite value calculated will be a combination of the product surface brightness as viewed by both the upstream and the downstream cameras. For example, if the upstream camera views the light stripe and records the greyscale value as 100 for some point within a particular bin's range, and the downstream camera records the greyscale value of 80 for another nearby point within the bin's range, then these points are summed into that bin as 180 and a count of 2 points.

If the product happens to be oriented in such a way as to produce a bright specular reflection as seen by one camera, then the product surface will generally be sloped away from the opposite camera, and the product will appear dimmer to that camera. Combining these views produces a composite greyscale value more representative of the actual surface brightness and less sensitive to specular reflection.

A typical value for a filter half-width W is 3, as illustrated in FIG. 5. A weighted greyscale value for a particular (x) coordinate then is calculated from the greyscale sum in the central bin corresponding to the (x) coordinate, and the sums in each of the three nearest bins on either side of the central bin. The weighting coefficient for the central bin in this case is 8; the coefficient for the two bins on either side is 4; for the next two outer bins 2; and the outer bins 1. The contribution of a bin to the weighted greyscale sum is the accumulated greyscale sum in the bin multiplied by the weighting coefficient.

If $G_i$ is the weighted greyscale sum for bin i, and $g_{i+j}$ the accumulated greyscale sum in bin i+j then:

$$G_i = \sum_{j=-W}^{+W} 2^{W-|j|} g_{i+j}$$

A weighted count $N^i$, equal to the sum of the products of the weighting coeffients and the sample $n_{i+j}$ in each bin i+j within W bins of the central bin i is also calculated:

$$N_i = \sum_{j=-W}^{+W} 2^{W-|j|} n_{i+j}$$

The final composite greyscale value for bin i is the weighted sum divided by the weighted count:

$$C_i = G_i/N_i$$

This filtering method interpolates a greyscale value for bins having no accumulated greyscale samples. The composite greyscale value $C_i$ is strongly influenced by any samples in the central bin, or in nearby bins, but a value will still be calculated entirely from data in more remote bins if it happens that nearby data is lacking.

By applying this filter to successive sets of greyscale data associated with (u, v) coordinate slices of the product, a complete greyscale map 28 of the product, indexed by (x) and (y) (cross-conveyor and along-conveyor coordinates, respectively) is assembled, as illustrated in FIG. 5. This map then is used in determining the cuts to be made on the product.

As the first step in calculating trim cuts, a greyscale threshold is calculated as a fraction of the average greyscale level of the entire product sample as represented in the greyscale map. Tentatively, cut paths are defined which follow the edge of the product a fixed distance in from the outer edge. Each point along these paths is then adjusted in the (x) direction outward toward the boundary of the product as long as the greyscale level is below the threshold value. If no bright areas are encountered, evidencing that there is no fat near the product periphery, then the cut path is moved until it lies outside the product boundary so that no cut is made.

In FIG. 5 it is to be noted that the exponential filter is symmetrical about the center element. In the illustration, the coefficient of the central element is 8 and the next adjacent coefficients are 4, the next outer coefficients are 2 and the outermost coefficients are 1. As illustrated in full line the filter is initially centered on bin 80, a point where there is lean meat, and at that point there are two values that have been accumulated in the bin; namely, one of 45 and another of 34, making the sum of 79. By weighting this sum by the coefficient 8 in the filter, the multiplied result is 632. Then, to the opposite sides of the central element the nearest bins have sums of 39 and 0 to the left and right respectively, then the next outer bins have sums of 31 and 150, and the outermost ones have sums of 43 and 78.

By multiplying each of the above sums by the corresponding coefficients in the filter, and adding up the multiplied results for each filter coefficient, the sum identified as $G_i$ is calculated to be 1271.

Next, the number of values in each bin is multiplied by the associated weighting coefficient, and the multiplied values are added together. Thus, starting from the left side of the filter shown in full lines, the numbers are $1 \times 1 + 1 \times 2 + 1 \times 4 + 2 \times 8 + 0 \times 4 + 2 \times 2 + 1 \times 1$, giving a weighted count of 28. By dividing the $G_i$ of 1271 by the $N_i$ of 28, the composite greyscale value identified as $C_i$ is determined to be 45.

The foregoing procedure is repeated sequentially by stepping the exponential filter 26 to the right to each succeeding bin associated with the product, as illustrated by the filter shown in broken line. These procedures provide composite greyscale values of 57, 69, 73 and 76 stepwise toward the right, for i=81, 82, 83, and 84. This shows that the data is darker on the left-hand side, corresponding with lean meat, and brighter on the right-hand side, corresponding with fat.

In actual practice the brightness of the belt surface is excluded so that it does not contribute to the values calculated for the fat areas. This is accomplished with simplicity since the boundary of the product is known from the height information obtained for determining the volume of slices. Thus, the number of values in each bin outward of the product is set to zero, thereby making a zero contribution to the $G_i$ and $N_i$.

The threshold level is based upon the overall average greyscale of the product. To illustrate, if the whole product is sampled and the average of the greyscale from all the collected data is the value of 100 out of a greyscale range of 0–255, it would be practicable to establish the threshold at 20% above the average, i.e. 120, and consider all points with greyscale values of 120 or higher to consist of fat rather than lean meat.

It is the composite greyscale $C_i$ values that are assembled in computer memory for controlling operation of the line-type cutters to remove peripheral areas of fat.

From the foregoing, it will be apparent that the present invention provides for the effective removal of fat from meat products, with minimum loss of lean meat, preliminary to reducing the meat product to portions of desired weight or shape. The method of this invention may be performed conveniently by use of the apparatus disclosed in the patents and patent applications identified hereinbefore, by the simple expedient of a computer program which identifies greyscale values of brightness of a line stripe as the latter scans a meat product moving on a conveyor belt. The program utilizes an exponential filter which is arranged to sweep across the bins containing image data of greyscale brightness, and utilizes the brightness values above a pre-selected threshold to control the line-type cutters to remove the areas of fat.

Although the exponential filter described hereinbefore is provided in the computer program, it may be provided as a physical component interfaced to the computer in the form of an integrated circuit arrangement configured to convert electric signals representing the brightness values of the pixels to electric signals representing the greyscale map 28 to which the threshold is applied in ascertaining the minimum level defining areas of fat. Such an arrangement is illustrated in FIG. 6.

Figure 6:
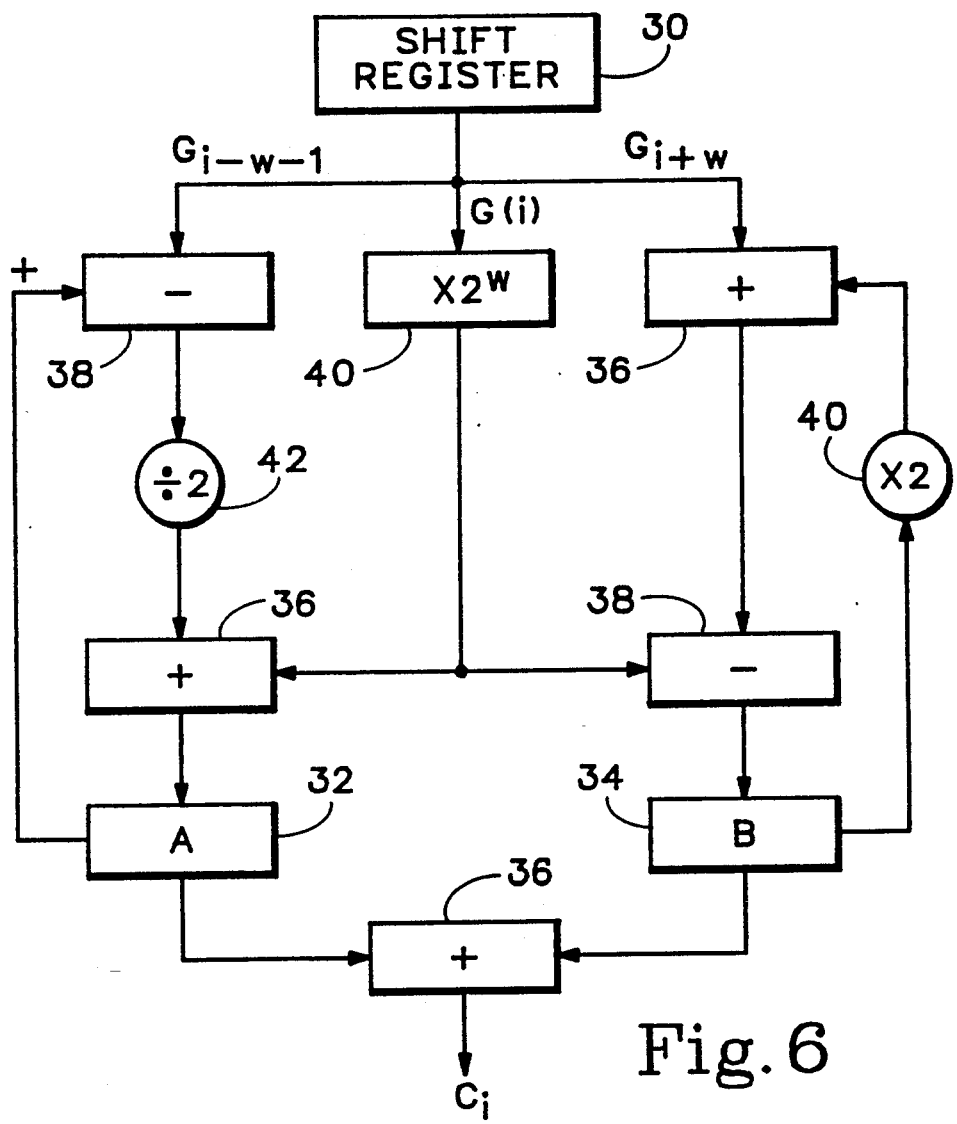
FIG. 6 is a schematic diagram of a digital electronic circuit which functions to provide an exponential filter for use in determining composite greyscale values.

FIG. 6 illustrates a digital electronic circuit that functions to calculate the values $G_i$ in sequence when presented at each step i with the brightness values $g_{i-w-1}$, $g_i$, and $g_{i+w}$. In the embodiment illustrated, these values are presented to the circuit from a tapped shift register 30.

The circuit includes two registers 32 and 34, designated A and B, respectively. For a 16 bit register, each of these registers may be provided by two integrated circuits available commercially as No. 74LS374. These registers hold partial sums from the most recently calculated value $G_{i-1}$. Register A holds the sum of the central filter term and trailing terms, i.e. terms with indices of i or less. Registry B holds the sum of the leading terms. Accordingly, the terms making up A become less influential in the result at the next step, while the terms making up B become more influential. If $A_{i-1}$ and $B_{i-1}$ represent the contents of registers A and B, respectively, at step i−1, then the next value $G_i$ is calculated as follows:

$$A_i = A_{i-1} - G_{i-w-1}/2 + 2^w G_i$$

$$B_i = 2B_{i-1} + G_{i+w} - 2^w G_i$$

$$G_i = A_i + B_i$$

The fundamental operations required in implementing the filter are addition, subtraction, multiplication by a power of 2 and division by a power of 2. The operations of addition and subtraction are achieved using commercially available integrated circuits. For example, additions may be achieved by addition components 36 formed of four integrated circuits available as No. 74LS283. Subtractions may be achieved by subtraction components 38 formed of two integrated circuits available as No. 74LS240 and four integrated circuits available as No. 74LS283. Multiplications and divisions by powers of 2 are achieved by multiplication components 40 and division components 42 which function by displacing a value's digits (bits) either to more significant positions in the case of multiplication, or to less significant positions in the case of division.

The circuit is initialized by clearing the registers A and B to zero and then calculating the values $G_{-w}, \ldots G_{-1}$ in sequence, using $g_i = 0$ where $i < 0$. Once this has been done, the values of interest $G_0, G_i, \ldots G_{n-1}$ corresponding to the available greyscale values may be calculated in sequence. When a non-existent greyscale value, i.e. $g_i$ where $i > n-1$ is called for, the value $g_i = 0$ is to be supplied.

It will be apparent that the values $N_i$ may be calculated using the circuit illustrated in FIG. 6 by substituting the greyscale counts $n_{i-w-1}$, $n_i$, and $n_{i+w}$ at each step in place of the greyscale values previously mentioned. To avoid the need for a memory to store the $G_i$ and $N_i$ for further processing, two identical circuits may be operated in parallel to generate $G_i$ and $N_i$ concurrently. The filtered greyscale value $C_i$ at each step then is calculated as $$C_i = G_i / N_i$$

This last division may be done either by a separate electronic divider circuit or as part of a software program in a computer interfaced with the circuit for the purpose of presenting input values to the circuit and retrieving the results.

The circuit illustrated in FIG. 6 exhibits the desirable characteristic that the time required to calculate each $G_i$ or $N_i$ is constant and independent of the filter half-width W. Thus, a greyscale map calculated using a large value W takes no longer to calculate than a map using a smaller value W.

It will be apparent to those skilled in the art that various changes may be made in the method described hereinbefore. For example, the configuration of the exponential filter may be modified as desired. Although the two camera system illustrated is preferred for the greater accuracy of image data collection, a single camera may be utilized if lesser accuracy is satisfactory. Although the method has been described herein for removing peripheral fat, it is also operable to remove areas of internal fat. The foregoing and other changes may be made, as desired, without departing from the spirit of this invention and the scope of the appended claims.

I claim:

1. The method of detecting and trimming fat from meat products, comprising:
   a) providing a stripe of light capable of spanning a meat product,
   b) moving a meat product on a support and the stripe of light one relative to the other,
   c) viewing the stripe of light on the meat product with at least one camera capable of converting spaced apart points of light of the light stripe to electric signals representing various magnitudes of grayscale brightness of said points of light,
   d) accumulating said electric signals,
   e) subjecting said accumulated electric signals to an exponential filter to convert said accumulated signals to a composite electric signal representing a composite grayscale value for each spaced apart point of light, and
   f) utilizing the composite electric signals representing brightness of points of light above a predetermined minimum brightness to operate a cutter to cut the meat product to remove the fat portion of said meat product that produced said points of light brightness above said minimum.

2. The method of claim 1 wherein the stripe of light is provided as a substantially vertical plane of white light.

3. The method of claim 1 wherein the stripe of light is stationary and the meat product is moved through the stripe of light on a support conveyor.

4. The method of claim 1 wherein the stripe of light is viewed by two cameras disposed on opposite sides of and substantially perpendicular to the stripe of light, and the electric signals from both cameras at each spaced apart point of light are accumulated and subjected to said exponential filter.

5. The method of claim 1 wherein the at least one camera is also capable of converting spaced apart points of light of the light stripe to electric signals representing heights of the upper surface of the meat product above the support, and the electric signals representing said heights are utilized to operate a line-type cutter to cut the meat product to portions of predetermined size.

6. The method of claim 1 wherein:
   a) the stripe of light is provided as a narrow sheet of white light,
   b) the stripe of light is stationary and the meat product is moved through the stripe of light on a support conveyor,
   c) the stripe of light is viewed by two cameras disposed on opposite sides of and substantially perpendicular to the stripe of light,
   d) each camera is also capable of converting spaced apart points of light of the light stripe to electric signals representing heights of the upper surface of the meat product above the support, and
   e) the electric signals representing said heights are utilized to operate a line-type cutter to cut the meat product to portions of predetermined size.

7. Apparatus for detecting and trimming fat from meat products, comprising:
   a) means for providing a stripe of light capable of spanning a meat product,
   b) meat product support means arranged for moving a meat product and the stripe of light one relative to the other,
   c) camera means for viewing the stripe of light on the meat product, the camera means being capable of converting spaced apart points of light of the light stripe to electric signals representing various magnitudes of grayscale brightness of said points of light, d) accumulator means associated with the camera means for receiving and accumulating said electric signals, e) exponential filter means for converting said accumulated electric signals to a composite electric signal representing a composite grayscale value for each spaced apart point of light, f) a cutter movable relative to the support means and operable to cut a meat product on said support, and g) control means for utilizing the electric signals representing grayscale brightness of points of light above a predetermined minimum brightness to operate the cutter to cut the meat product to remove the fat portion of said meat product that produced said points of light brightness above said minimum.

8. The apparatus of claim 7 wherein the means for providing the stripe of light is a source providing a substantially vertical plane of white light.

9. The apparatus of claim 7 wherein the means for providing the stripe of light is stationary and the support means is a conveyor for moving a meat product through the stripe of light on the conveyor.

10. The apparatus of claim 7 wherein the camera means includes two cameras disposed on opposite sides of and substantially perpendicular to the stripe of light, said cameras communicating with said accumulator means for accumulating the electric signals from both cameras at each of the spaced apart points of light of the light stripe.

11. The apparatus of claim 7 wherein the cutter is a line-type cutter, the camera means is also capable of converting spaced apart points of light of the light stripe to electric signals representing heights of the upper surface of the meat product above the support means, and the electric signals representing said heights are utilized to operate the line-type cutter to cut the meat product to portions of predetermined size.

12. The apparatus of claim 7 wherein:
a) the means for providing the stripe of light is a source providing a substantially vertical plane of white light,
b) the means for providing the stripe of light is stationary and the support means is a conveyor for moving a meat product through the stripe of light on the conveyor,
c) the camera means includes two cameras disposed on opposite sides of and substantially perpendicular to the stripe of light,
d) each camera is also capable of converting spaced apart points of light of the light stripe to electric signals representing heights of the upper surface of the meat product above the support conveyor,
e) the cutter is a line-type cutter movable relative to the support means, and
f) the electric signals representing said heights are utilized to operate the line-type cutter to cut the meat product to portions of predetermined size.

* * * * *